United States Patent
Gustafson et al.

(10) Patent No.: US 8,489,418 B2
(45) Date of Patent: Jul. 16, 2013

(54) SYSTEM AND METHODS FOR REFERRING PHYSICIANS BASED ON HIERARCHICAL DISEASE PROFILE MATCHING

(75) Inventors: Steven Matt Gustafson, Niskayuna, NY (US); Matthew Cardoso, Boston, MA (US)

(73) Assignee: General Electric Company, Schenectady, NY (US)

( * ) Notice: Subject to any disclaimer, the term of this patent is extended or adjusted under 35 U.S.C. 154(b) by 223 days.

(21) Appl. No.: 12/982,365

(22) Filed: Dec. 30, 2010

(65) Prior Publication Data
US 2012/0173280 A1 Jul. 5, 2012

(51) Int. Cl.
*G06Q 10/00* (2012.01)

(52) U.S. Cl.
USPC .................................................. 705/2; 705/3

(58) Field of Classification Search
USPC .......................................................... 705/2–3
See application file for complete search history.

(56) References Cited

U.S. PATENT DOCUMENTS

| | | | |
|---|---|---|---|
| 7,383,197 B1 | 6/2008 | Neuman | |
| 7,401,028 B2 | 7/2008 | Deakter | |
| 7,558,738 B1 * | 7/2009 | Flatt | 705/2 |
| 7,580,846 B2 | 8/2009 | Chishti et al. | |
| 7,640,173 B2 | 12/2009 | Surpin et al. | |
| 7,702,524 B1 * | 4/2010 | Whibbs et al. | 705/2 |
| 7,756,721 B1 | 7/2010 | Falchuk et al. | |
| 7,761,308 B2 | 7/2010 | Falchuk et al. | |
| 7,809,601 B2 | 10/2010 | Shaya et al. | |
| 7,818,183 B2 * | 10/2010 | Schoenberg | 705/2 |
| 2009/0198509 A1 * | 8/2009 | Dumoff | 705/2 |

FOREIGN PATENT DOCUMENTS

WO WO 00/57326 * 9/2000

OTHER PUBLICATIONS

Medical News Today, "Fewer Patients Using Health Care Provider Quality Ratings Web Sites to Make Decisions", webpage: medicalnewstoday, Dec. 3, 2008, 1 page.*

* cited by examiner

*Primary Examiner* — Michael Fuelling
(74) *Attorney, Agent, or Firm* — Hanley, Flight & Zimmerman, LLC

(57) ABSTRACT

Systems, apparatus, and methods for referring physicians based on hierarchical disease profile matching are disclosed. An example system includes a data store to include a plurality of disease profiles, each disease profile associated with a patient condition, a user interface to accept a user request for a referral of a patient to a physician, and a referral processor to compare a profile associated with the patient including a patient symptom to the plurality of disease profiles to generate one or more physician recommendations for referral, the referral processor to refine the one or more physician recommendations based on one or more characteristics associated with each of the one or more physician recommendations, the referral processor to provide the refined one or more physician recommendations to a user for review and selection via the user interface.

4 Claims, 4 Drawing Sheets

SYSTEM AND METHODS FOR REFERRING PHYSICIANS BASED ON HIERARCHICAL DISEASE PROFILE MATCHING

FIELD OF THE DISCLOSURE

This disclosure relates generally to physician referrals and, more particularly, to systems and methods for referring physicians to patients based on profile matching.

BACKGROUND

Health Management Organizations (HMOs) and other Accountable Care Organizations have a pool of possible physicians from which to refer a patient. Physician referral systems enable the best possible candidate physicians to be automatically and quickly identified from this pool. A good physician referral system will make the most of relevant profile data associated with the patient as well as the physicians. Such data can be divided into different categories that will enable health services to be delivered efficiently at low cost.

BRIEF SUMMARY

Example systems, apparatus, and methods to generate a recommendation list of physicians to a patient are disclosed. An example system includes a data store to include a plurality of disease profiles, each disease profile associated with a patient condition, a user interface to accept a user request for a referral of a patient to a physician, a referral processor to compare a profile associated with the patient including a patient symptom to the plurality of disease profiles to generate one or more physician recommendations for referral, the referral processor to refine the one or more physician recommendations based on one or more characteristics associated with each of the one or more physician recommendations, the referral processor to provide the refined one or more physician recommendations to a user for review and selection via the user interface.

An example method includes generating physician referral recommendations for a patient, the method comprising categorizing physicians in an organization by department and specialty, classifying and assembling disease profiles for common diseases, determining a disease profile for a patient, identifying a group of one or more categorized physicians matching the disease profile of the patient, refining the group of one or more categorized physicians associated with the patient disease profile based on one or more features associated with each physician in the group, generating a recommendation of one or more physicians, and providing the recommendation of one or more physicians to a user for review and selection.

An example method comprises selecting a patient, matching the patient to a patient condition profile, the patient condition profile associated with a patient health condition, retrieving a group of one or more physicians based on the patient condition profile, refining the group of one or more physicians associated with the patient condition profile based on one or more features associated with each physician in the group, generating a recommendation of one or more physicians, and providing the recommendation of one or more physicians to a user for review and selection.

An example apparatus includes a tangible computer readable storage medium including executable program instructions which, when executed by a computer processor, cause the computer to implement a method of generating physician referral recommendations for a patient. The example method includes generating physician referral recommendations for a patient, the method comprising categorizing physicians in an organization by department and specialty, classifying and assembling disease profiles for common diseases, determining a disease profile for a patient, identifying a group of one or more categorized physicians matching the disease profile of the patient, refining the group of one or more categorized physicians associated with the patient disease profile based on one or more features associated with each physician in the group, generating a recommendation of one or more physicians, and providing the recommendation of one or more physicians to a user for review and selection.

Figure 1:
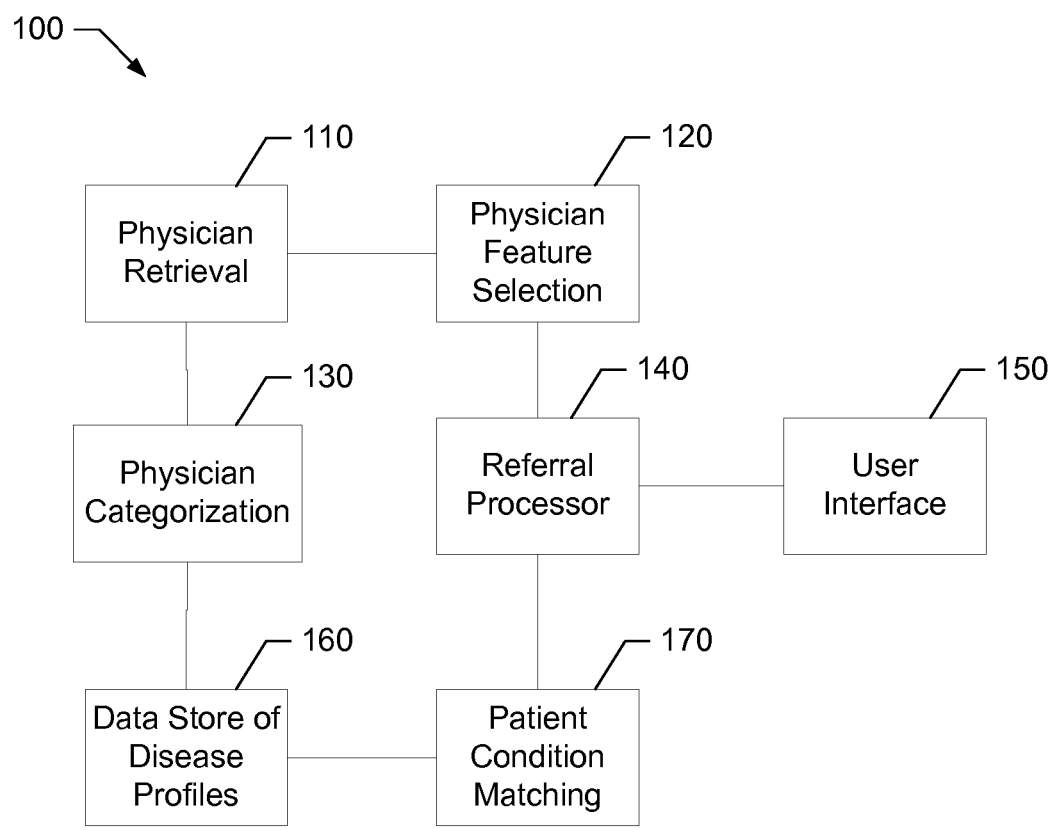
FIG. 1 illustrates an exemplary physician referral system in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION

Although the following discloses example systems and methods including, among other components, software executed on hardware, it should be noted that such methods and apparatus are merely illustrative and should not be considered as limiting. For example, it is contemplated that any or all of these hardware and software components could be embodied exclusively in hardware, exclusively in software, exclusively in firmware, or in any combination of hardware, software, and/or firmware. Accordingly, while the following describes example systems and methods, the examples provided are not the only way to implement such methods and systems.

When any of the appended claims are read to cover a purely software and/or firmware implementation, at least one of the elements in an at least one example is hereby expressly defined to include a tangible medium such as a memory, DVD, CD, Blu-ray, etc. storing the software and/or firmware.

Currently, the selection of physicians for referrals is made manually using a variety of heuristics and ad-hoc methods. Since outcomes and cost features are rarely available in highly quantitative forms, it is thought that social networks and scheduling are often the biggest drivers of referrals. However, as the use of more electronic medical records (EMR) systems is increasing, health care performance data is becoming more available. Additionally, as different pay models are likely to be developed, it will be more important for healthcare organizations to be able to monitor, control and select physicians based on a quantitative data. In certain examples, recommendation algorithms, such as physician recommendation algorithms, allow users with an efficient, automated way to sort through and analyze available data to the benefit of users and patients.

Certain examples provide systems, apparatus, and methods for "intelligent" physician referral resulting in better care at lower cost to patient and provider. Cost can be represented as a function of time to treat a patient, the number of appointments necessary, the number of imaging required, tests, and post-treatment follow-up appointments, for example. Physician referral algorithms can be a differentiating feature for EMR products to help provide improvement in care outcomes and efficiency, enhancing their value. Ultimately, these systems and associated methods enable the best candidate physicians to be automatically identified so that a patient can more easily make informed decisions such that health care is delivered more efficiently to the patient based on outcome and cost.

Certain examples disclosed herein enable generation of a recommendation list of physicians from which a patient can choose. The list is generated by considering data related to the patient and physician, including performance data for the physicians. Other factors that are considered by the algorithm include the categories of treatment the physicians usually engage in, as well as additional features of the physician and a general patient condition profile. Patient feedback, as well as expertise, can be considered when generating and narrowing the list, for example. Once the patient selects a physician from the list, the physician can opt to provide care to the patient or not.

FIG. 1 illustrates an example physician referral system 100. The example physician referral system 100 of FIG. 1 includes physician retrieval 110, physician feature selection 120, physician categorization 130, a referral processor 140, a user interface 150, a data store of disease profiles 160, and patient condition matching 170. To maintain a repository of common diseases that an organization is likely to see, the example physician referral system 100 contains a data store of disease and/or other patient condition profiles 160. While a profile in the data store 160 can include one or more of a disease and/or other patient complaint, condition, disorder, demographic, etc., the profiles will be referred to herein as disease profiles. However, it is understood that, in various examples, the profiles can include more than a disease recitation or description.

For example, a pre-diabetic disease profile is created for patients that are considered to be pre-diabetic based on two factors such as weight and blood glucose levels, and another disease profile for pre-diabetic is based on three or more factors including weight, hypertension and family history. The example data store of disease profiles 160 aggregates these profiles into a database. To categorize physicians into areas that they are most likely to able to treat well, the example physician referral system 100 includes physician categorization 130. Examples of physician categorization 130 include internal medicine, endocrinology, and/or cardiology. To assign a patient to a particular disease profile, the example physician referral system 100 includes patient condition matching 170. The example patient condition matching 170 enables a patient, when selected, to receive a referral to a physician, based on matching, within a level of tolerance, the patient to the closest disease profile within the data store of disease profiles 160. To retrieve the physician(s) matching the profile, the example physician referral system 100 includes physician retrieval 110. Upon patient condition matching 170, the example physician retrieval 110 is used to reduce the pool of possible physicians to those who also match the patient's disease profile. If there is no match, then physician categorization 130 is further used to select a physician category, going as deep into the hierarchy of categories as possible based on the symptoms.

To further refine the list of possible physicians, the example physician referral system 100 includes physician feature selection 120. An example physician feature selection 120 examines other characteristics of the physician such as past performance, outcome, cost, and efficiency of treating patients. Other characteristics of physician feature selection 120 include availability and geographic location. Physician feature selection 120 can also be combined with features of the patient, such as their willingness to wait or travel. To finally generate the list of physicians, the example physician referral system 100 includes a referral processor 140. The example referral processor 140 uses one or more of the above named factors, in addition to pre-selected options specified by a user, to generate the recommendation list of candidate physicians from which to refer the patient.

To enable the user to interact with the system, the example physician referral system 100 includes a user interface 150. The example user interface 150 enables a health care staff member to provide the list to the patient. If there is no recommendation at all, then the referral would be made by traditional means.

As used herein, the term tangible computer-readable medium is expressly defined to include any type of computer-readable medium and to expressly exclude propagating signals. Example computer-readable medium include, but are not limited to, a volatile and/or non-volatile memory, a volatile and/or non-volatile memory device, a compact disc (CD), a digital versatile disc (DVD), a floppy disk, a read-only memory (ROM), a random-access memory (RAM), a programmable ROM (PROM), an electronically-programmable ROM (EPROM), an electronically-erasable PROM (EEPROM), an optical storage disk, an optical storage device, magnetic storage disk, a magnetic storage device, a cache, and/or any other storage media in which information is stored for any duration (e.g., for extended time periods, permanently, brief instances, for temporarily buffering, and/or for caching of the information) and which can be accessed by a processor, a computer and/or other machine having a processor, such as the example processor platform P100 discussed below in connection with FIG. 4. As used herein, the term non-transitory computer-readable medium is expressly defined to include any type of computer-readable medium and to exclude propagating signals.

While an example physician referral system 100 is illustrated in FIG. 1, one or more of the elements, processes and/or devices illustrated in FIG. 1 may be combined, divided, rearranged, omitted, eliminated and/or implemented in any other way. Further, the example physician retrieval 110, the example physician feature selection 120, the example physician categorization 130, the example referral processor 140, the example user interface 150, the example data store of disease profiles 160, and/or the example patient condition matching 170 may be implemented by hardware, software, firmware and/or any combination of hardware, software and/or firmware. Thus, for example, any of example physician retrieval 110, the example physician feature selection 120, the example physician categorization 130, the example referral processor 140, the example user interface 150, the example data store of disease profiles 160, and/or the example patient condition matching 170 could be implemented by the example processor platform P100 of FIG. 4 and/or one or more circuit(s), programmable processor(s), application specific integrated circuit(s) (ASIC(s)), programmable logic device(s) (PLD(s)) and/or field programmable logic device(s) (FPLD(s)), field-programmable gate array(s) (FPGA(s)), fuses, etc. When any apparatus claim of this patent incorporating one or more of these elements is read to cover a purely software and/or firmware implementation, at least one of the example physician retrieval 110, the example physician feature selection 120, the example physician categorization 130, the example referral processor 140, the example user interface 150, the example data store of disease profiles 160, and/or the example patient condition matching 170 are hereby expressly defined to include a tangible article of manufacture such as a tangible computer-readable medium storing the firmware and/or software. Further still, any of the example physician retrieval 110, the example physician feature selection 120, the example physician categorization 130, the example referral processor 140, the example user interface 150, the example data store of disease profiles 160, and/or the example patient condition matching 170 may include one or more elements, processes and/or devices in addition to, or instead of, those illustrated in FIG. 1, and/or may include more than one of any or all of the illustrated elements, processes and devices.

Figure 2:
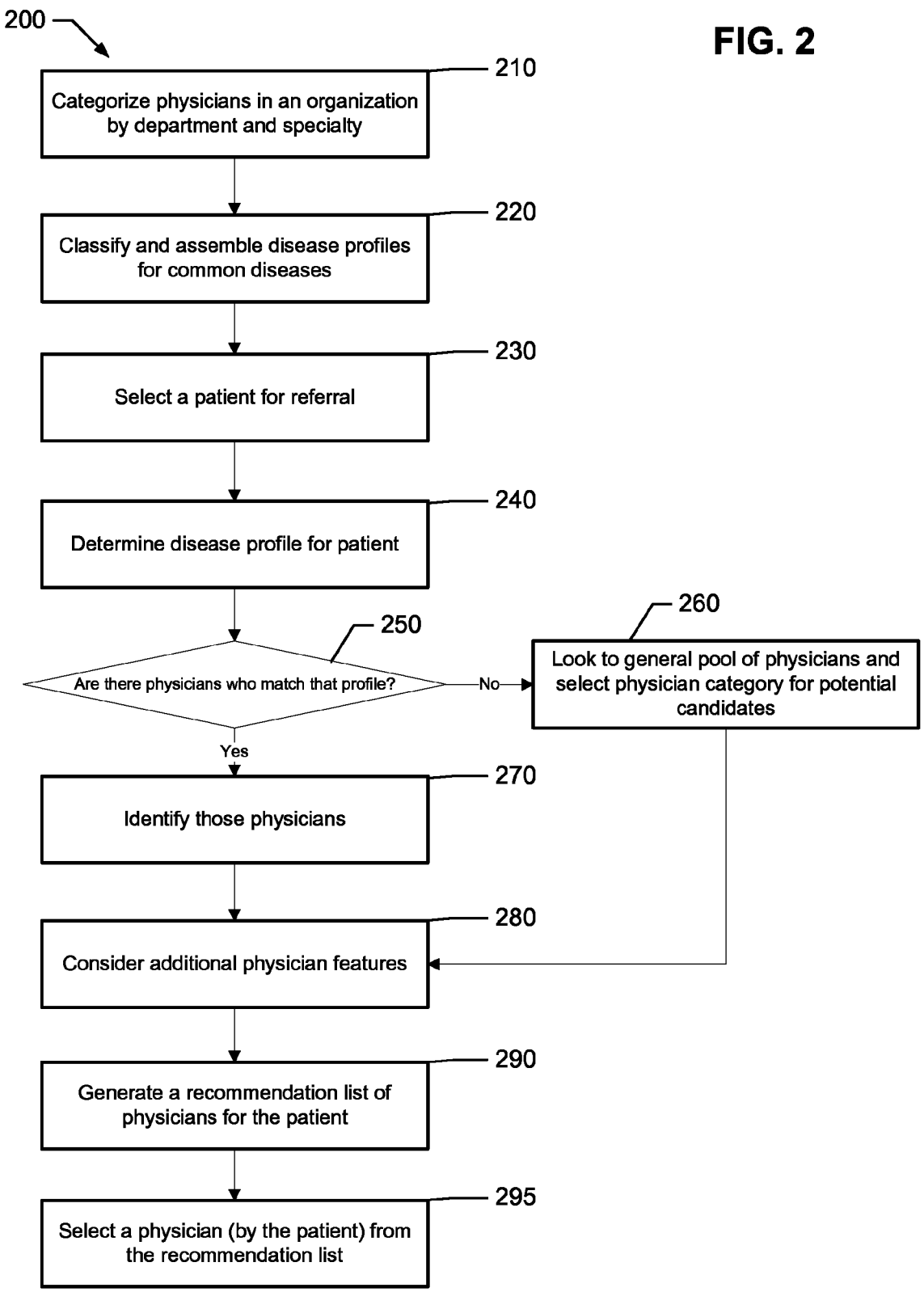
FIG. 2 illustrates a flowchart representative of an example method of referring physicians to patients based on physician categorization and disease profiles.

FIG. 2 is a flowchart representing an example process that may be embodied as machine-accessible instructions and executed by, for example, one or more processors to generate a list of candidate physicians. A processor, a controller and/or any other suitable processing device may be used, configured and/or programmed to perform the example processes of FIG. 2. For example, the process of FIG. 2 may be embodied in coded instructions stored on a tangible computer-readable medium. Machine-readable instructions comprise, for example, instructions that cause a processor, a computer and/or a machine having a processor to perform one or more particular processes. Alternatively, some or all of the components of the example process of FIG. 2 may be implemented using any combination(s) of ASIC(s), PLD(s), FPLD(s), FPGA(s), fuses, discrete logic, hardware, firmware, etc. Also, some or all of the components of the example process of FIG. 2 may be implemented manually or as any combination of any of the foregoing techniques, for example, any combination of firmware, software, discrete logic and/or hardware. Further, many other methods of implementing the example operations of FIG. 2 may be employed. For example, the order of execution of the blocks may be changed, and/or one or more of the blocks described may be changed, eliminated, sub-divided, or combined. Additionally, the blocks of any or all of the components of the example process of FIG. 2 may be carried out sequentially and/or carried out in parallel by, for example, separate processing threads, processors, devices, discrete logic, circuits, etc.

The example process 200 of FIG. 2 begins with physicians being categorized in an organization by department and specialty (block 210). The categorization is hierarchical going from general categories down to specialists. Example categories can be, for example, pediatrics, radiology, etc. The example process 200 of FIG. 2 classifies and assembles disease profiles (block 220). The disease profiles are created for the most common types of diseases an organization sees. A patient is selected for referral (block 230) and is one of many patients looking for services. For the patient that is selected, the example process of FIG. 2 determines his/her disease profile (block 240). Disease profiles for diabetics can include factors such as weight, blood glucose levels, hypertension, family history, etc. The process 200 of FIG. 2 determines whether there are any physicians who match that profile (250). If there is a match, those physicians are identified (block 270). If not, then the example process 200 looks to the general pool of physicians and selects a physician category for potential candidates (block 260). In both cases, additional physician features are considered (block 280) such as past performance, availability, geographic location, and/or price. The example process 200 of FIG. 2 generates a recommendation list of physicians for the patient (block 290). The user (e.g., a patient, administrator, referring physician, etc.) can select a physician from the recommendation list (block 295).

In certain examples, selection of a physician initiates an email, message, and/or appointment scheduling with the selected physician and/or associated administrator. In certain examples, a physician may be automatically selected for the patient. In such examples, the automatic selection may be overridden by a user (e.g., a physician). In certain examples, the user is guided through a referral process once a physician is selected from the recommendation list. The selected physician is sent a referral request that he/she can accept or deny. If the physician accepts, then that physician starts the appointment/scheduling process with the patient, for example.

Figure 3:
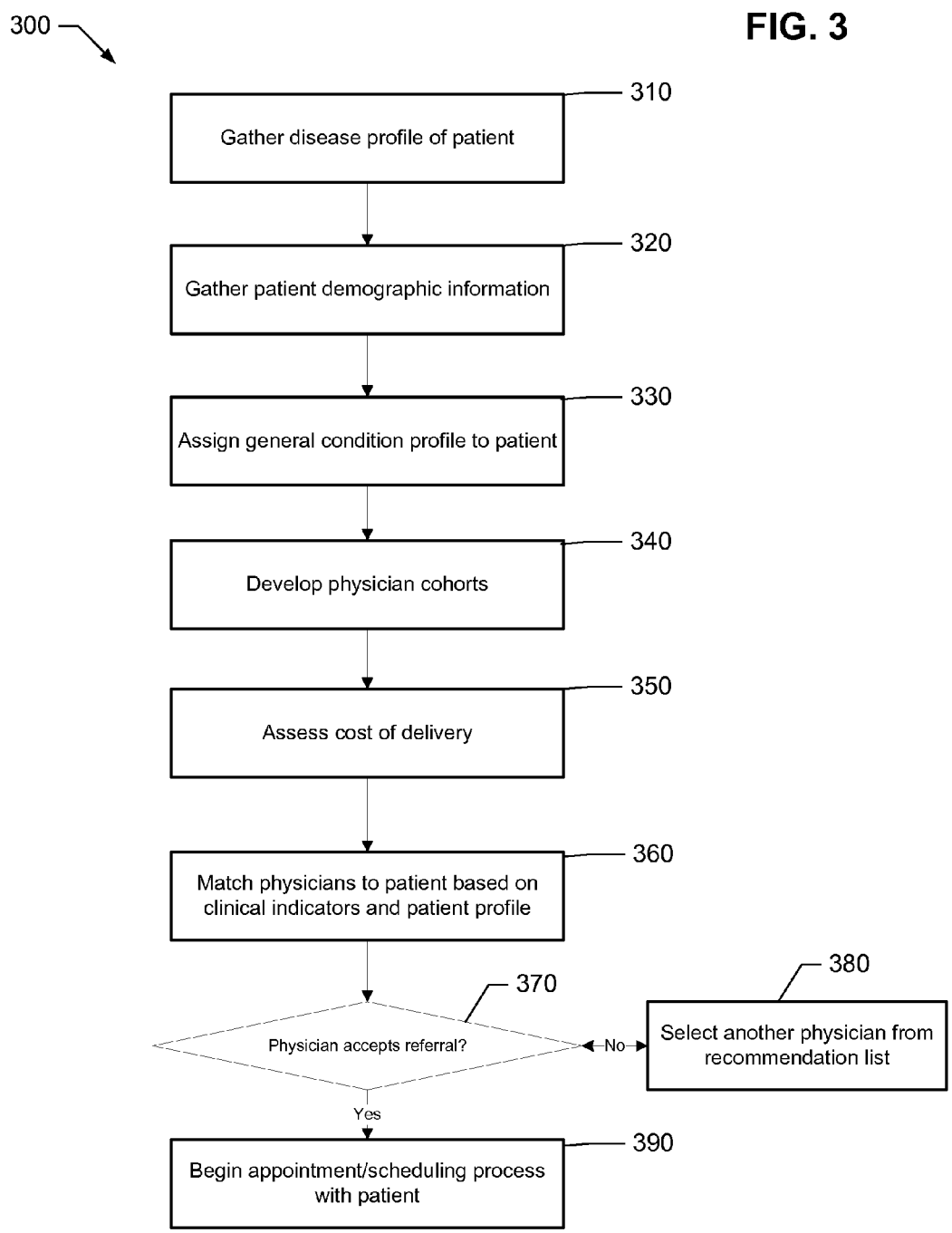
FIG. 3 illustrates a flowchart representative of an example method of referring physicians to patients based on matching physicians to a patient condition profile.

FIG. 3 is a flowchart representing an example process that may be embodied as machine-accessible instructions and executed by, for example, one or more processors to generate a list of candidate physicians. A processor, a controller and/or any other suitable processing device may be used, configured and/or programmed to perform the example processes of FIG. 3. For example, the process of FIG. 3 may be embodied in coded instructions stored on a tangible computer-readable medium. Machine-readable instructions comprise, for example, instructions that cause a processor, a computer and/or a machine having a processor to perform one or more particular processes. Alternatively, some or all of the components of the example process of FIG. 3 may be implemented using any combination(s) of ASIC(s), PLD(s), FPLD(s), FPGA(s), fuses, discrete logic, hardware, firmware, etc. Also, some or all of the components of the example process of FIG. 3 may be implemented manually or as any combination of any of the foregoing techniques, for example, any combination of firmware, software, discrete logic and/or hardware. Further, many other methods of implementing the example operations of FIG. 3 may be employed. For example, the order of execution of the blocks may be changed, and/or one or more of the blocks described may be changed, eliminated, sub-divided, or combined. Additionally, the blocks of any or all of the components of the example process of FIG. 3 may be carried out sequentially and/or carried out in parallel by, for example, separate processing threads, processors, devices, discrete logic, circuits, etc.

The example process 300 of FIG. 3 generally looks at physicians based on disease profiles and physician features, but not necessarily physician categories since a physician may have achieved good results and gotten good feedback outside of his/her specialty area. Physicians within an organization can be associated with a disease profile, but may not necessarily be categorized by department. The example process 300 of FIG. 3 begins by gathering the disease profile of the patient (block 310) as well as the demographic information of the patient (block 320). Based on both sets of information, the example process 300 of FIG. 3 assigns a general condition profile to the patient (block 330). With this information, the example process 300 of FIG. 3 develops physician cohorts (block 340). In addition to looking at the general patient condition profile, the example process of FIG. 3 assesses the cost of delivery (block 350). Physicians are matched to the patient based on clinical indicators and the patient profile (block 360). In this process 300, a physician is judged based on the patient condition profiles. For instance, a physician may be a cardiologist, but if he/she sees a lot of diabetics and maintains quality very well, then he/she may be selected. The example process 300 helps identify the best provider(s) for the patient without putting him/her into a category. If the physician accepts the referral when the patient chooses him/her (block 370), then the process 300 of FIG. 3 begins an appointment/scheduling process (block 390). If not, then another physician is selected from the recommendation list (block 380).

Figure 4:
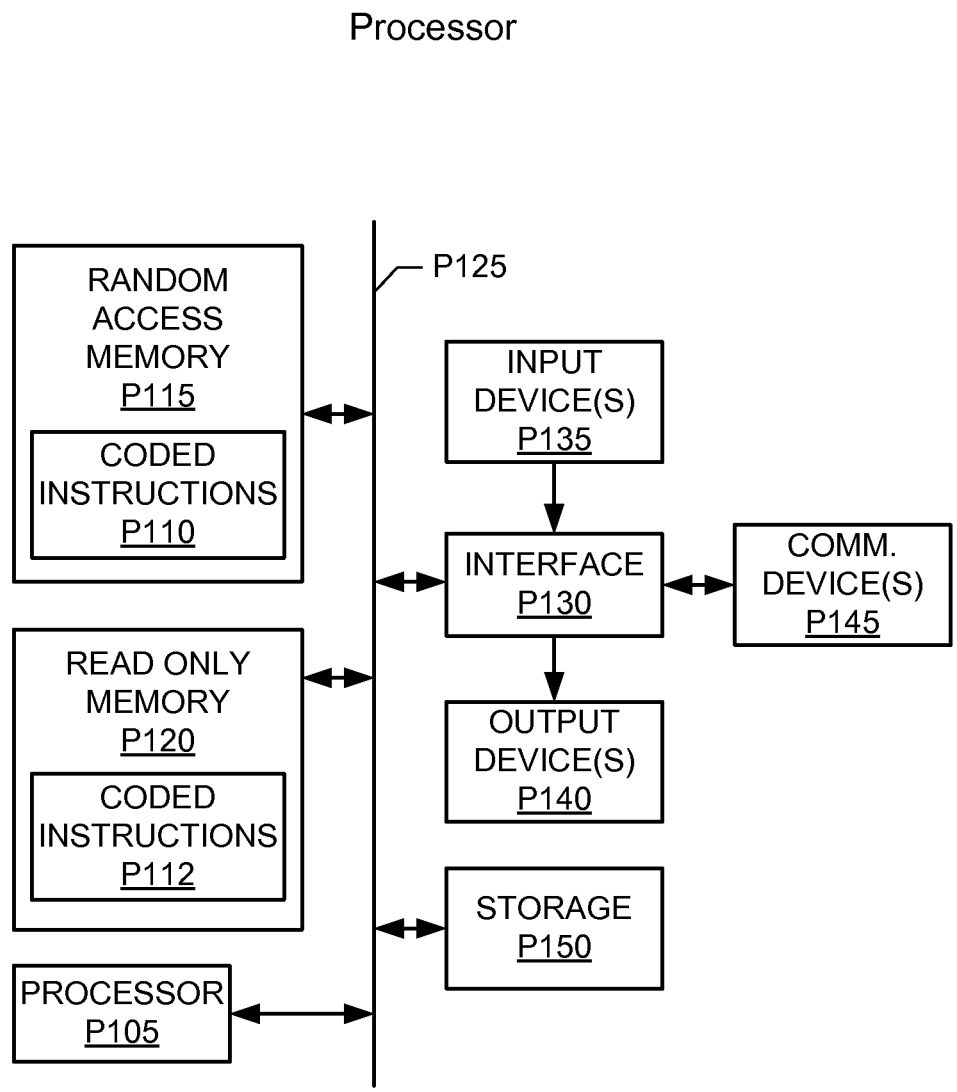
FIG. 4 is a schematic illustration of an example processor platform that may be used and/or programmed to implement any or all of the disclosed examples to refer physicians to patients.

FIG. 4 is a block diagram of an example processor platform P100 capable of executing the example process of FIG. 2 and the example process of FIG. 3 to generate a recommendation list of referrals for patients to select from. The example processor platform P100 can be, for example, a computer, a workstation, a server and/or any other type of computing device containing a processor.

The processor platform P100 of the instant example includes at least one programmable processor P105. For example, the processor P105 can be implemented by one or more Intel® microprocessors from the Pentium® family, the Itanium® family or the XScale® family. Of course, other processors from other processor families and/or manufacturers are also appropriate. The processor P105 executes coded instructions P110 and/or P112 present in main memory of the processor P105 (e.g., within a volatile memory P115 and/or a non-volatile memory P120) and/or in a storage device P150. The processor P105 may execute, among other things, the example machine-accessible instructions of FIGS. 2-3 to generate a recommendation list of physicians for patients to select from. Thus, the coded instructions P110, P112 may include the example instructions of FIGS. 2-3.

The processor P105 is in communication with the main memory including the non-volatile memory P110 and the volatile memory P115, and the storage device P150 via a bus P125. The volatile memory P115 may be implemented by Synchronous Dynamic Random Access Memory (SDRAM), Dynamic Random Access Memory (DRAM), RAMBUS Dynamic Random Access Memory (RDRAM) and/or any other type of RAM device. The non-volatile memory P110 may be implemented by flash memory and/or any other desired type of memory device. Access to the memory P115 and the memory P120 may be controlled by a memory controller.

The processor platform P100 also includes an interface circuit P130. Any type of interface standard, such as an external memory interface, serial port, general-purpose input/output, as an Ethernet interface, a universal serial bus (USB), and/or a PCI express interface, etc, may implement the interface circuit P130.

The interface circuit P130 may also includes one or more communication device(s) P112 such as a network interface card to facilitate exchange of data, packets, and/or routing information with other nodes, servers, devices and/or routers of a network.

In some examples, the processor platform P100 also includes one or more mass storage devices P150 to store software and/or data. Examples of such storage devices P150 include a floppy disk drive, a hard disk drive, a solid-state hard disk drive, a CD drive, a DVD drive and/or any other solid-state, magnetic and/or optical storage device. The example storage devices P150 may be used to, for example, store the example coded instructions of FIGS. 2-3.

Thus, certain examples provide a way to generate a recommended list of physicians to a patient. This is done automatically and quickly and is meant to provide the best list of possible physicians matching the condition of the patient. The list is based on a number of factors including convenience and location and helps enable a user generating the recommendation list to navigate forward to narrow a recommendation list and/or backward to broaden the list. Certain examples transform a pool of possible physicians into a refined ranking of physicians. Physicians that are not eliminated by the constraining information, rules, preferences, etc., can be ranked and sorted. Additionally, in certain examples, a pareto-front can be calculated to return the physician(s) that have the most attractive values per feature across all features. A physician that is very efficient in treating previous patients can be farther away than another physician, but ultimately ranked higher because of their past performance. All features/parameters can be combined to return a ranked list of physicians, which has the ability to be further sorted independently by an end user.

In certain examples, clinical decisioning is provided to collect information and best practices regarding how clinicians have treated patients in the past and apply that information to a current patient. An organization requesting a referring can specify one or more parameters/criteria to frame a referral request. For example, an organization might say that they want to refer patients to physicians who treat patients faster using fewer resources. In certain examples, patients with similarities can be grouped to make more efficient use of expertise, resources, etc. By tailoring priorities and/or other parameters, as well as focusing on profiles, categories, and available information to narrow a list of referral physicians, an organization can be provide with more control of outcomes and cost and better management of resources, for example.

In certain examples, based on preference and information captured regarding physicians, diseases, cost, and/or other data, a healthcare organization can be provided with a list of recommendations for referral. Data can be gathered from one or more data sources including clinical knowledge bases, clinical information systems, patient and/or colleague feedback, review/processing of clinical outcomes data, financial and/or schedule analysis, etc. For an accountable care organization, rather than referrals being given to patients based on physician relationships, certain examples provide greater efficiency by matching patient to physician based on these indicators, not based on friends and/or other personal relationships that may run counter to diagnosis and treatment efficiency and effectiveness goals. Certain examples help a referring physician to deliver a better referral based not only on quality but also on a finer grain of detail regarding physician suitability for a particular physician. For example, a physician may have a history of working well with poor diabetics and not with wealthy suburban housewives. A physician can be evaluated based on patient profile. For example, the physician may be a cardiologist, but if he sees many diabetics and maintains a high quality of treatment, then he may be selected. In this way, a best care provider for a patient can be identified without putting the care provider into a category.

In certain examples, available data is analyzed to identify and establish profiles and then develop cohorts based on the profiles that would then include the profiles. Specific type(s) of cohorts can be examined based on relevance (e.g., disease state, primary physician referral cost, etc.) to identify and narrow a referral recommendation list. Additionally, medical literature, common morbidity profiles, etc., can be referenced in comparison with patient condition and physician information to develop a referral list. Physician(s) can be matched with patients based on clinical indicators as well as demographics and/or other factors, for example.

Although certain example methods, apparatus and articles of manufacture have been described herein, the scope of coverage of this patent is not limited thereto. On the contrary, this patent covers all systems, methods, apparatus and articles of manufacture fairly falling within the scope of the claims of this patent.

What is claimed is:

1. A computer-implemented method of generating physician referral recommendations for a patient, the method comprising:

categorizing, physicians in an organization by department and specialty to form one or more groups of one or more categorized physicians; and classifying and assembling disease profiles for a plurality of diseases; and determining a disease profile for a patient based on a patient condition profile associated with the patient; and identifying, using a processor, a group of one or more categorized physicians matching the disease profile of the patient; and refining, using the processor, the group of one or more categorized physicians associated with the patient disease profile based on one or more features associated with each physician in the group, the one or more features associated with each physician comprising physician performance data including one or more of the physician's patient treatment history, patient feedback, clinical outcome data, and expected cost of delivery including financial and schedule analysis associated with the physician; and generating, using the processor, a recommendation of one or more physicians based on the refined group of one or more categorized physicians; and providing the recommendation of one or more physicians to a user for review and selection.

2. The method of claim 1, wherein generating the recommendation of one or more physicians comprises scoring each physician based on an association with the patient condition profile and the physician's features.

3. The method of claim 1, wherein generating the recommendation of one or more physicians takes into account a cost of delivery.

4. The method of claim 1, further comprising creating disease profiles for one or more types of diseases.

* * * * *